(12) United States Patent
Chichetto

(10) Patent No.: US 10,869,775 B1
(45) Date of Patent: Dec. 22, 2020

(54) SACROILIAC MANIPULATION SYSTEM

(71) Applicant: Luke E. Chichetto, Winter Haven, FL (US)

(72) Inventor: Luke E. Chichetto, Winter Haven, FL (US)

( * ) Notice: Subject to any disclaimer, the term of this patent is extended or adjusted under 35 U.S.C. 154(b) by 406 days.

(21) Appl. No.: 15/927,215

(22) Filed: Mar. 21, 2018

(51) Int. Cl.
*A61F 5/01* (2006.01)
*A61F 5/02* (2006.01)
*A61B 17/70* (2006.01)

(52) U.S. Cl.
CPC .......... *A61F 5/028* (2013.01); *A61B 17/7055* (2013.01); *A61B 17/7032* (2013.01); *A61B 17/7062* (2013.01); *A61F 5/0193* (2013.01)

(58) Field of Classification Search
CPC ............ A61B 17/7055; A61B 17/7032; A61B 17/7062; A61B 17/7011; A61B 17/7049; A61F 5/0102; A61F 5/028; A61F 5/0193; A61F 5/37; A61F 5/3715; A63B 2023/006; A63B 23/04; A63B 21/4011
USPC ....................... 128/846, 869, 876, 882; 602/5
See application file for complete search history.

(56) References Cited

U.S. PATENT DOCUMENTS

| | | | | |
|---|---|---|---|---|
| 4,390,015 | A | * | 6/1983 | Clements .................. A61F 5/01 128/882 |
| 4,608,971 | A | * | 9/1986 | Borschneck .......... A61F 5/0585 602/23 |
| 7,789,815 | B2 | * | 9/2010 | An ........................ A63B 21/023 482/126 |
| 2008/0078409 | A1 | * | 4/2008 | Ciccantelli ............ A61F 5/0193 128/845 |

* cited by examiner

*Primary Examiner* — Rachael E Bredefeld
*Assistant Examiner* — William T Kao

(57) ABSTRACT

A base has an upwardly facing surface and a downwardly facing surface, an interior edge and an exterior edge, and a first end and a second end. The base has a central section in a rectangular configuration. The base has a first end section in a semi-cylindrical configuration. The first end section extends between the first end and the central section. The base has a second end section in a semi-cylindrical configuration. The second end section extends between the second end and the central section. First and second hook and loop patches are on the first and second end sections. First and second hook and loop straps each have a fixed end attached to the central section. Each hook and loop strap has a free end separably coupled to an associated hook and loop patch.

4 Claims, 4 Drawing Sheets

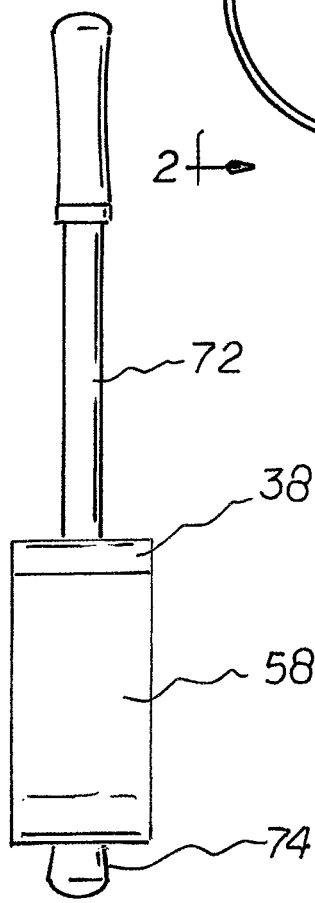
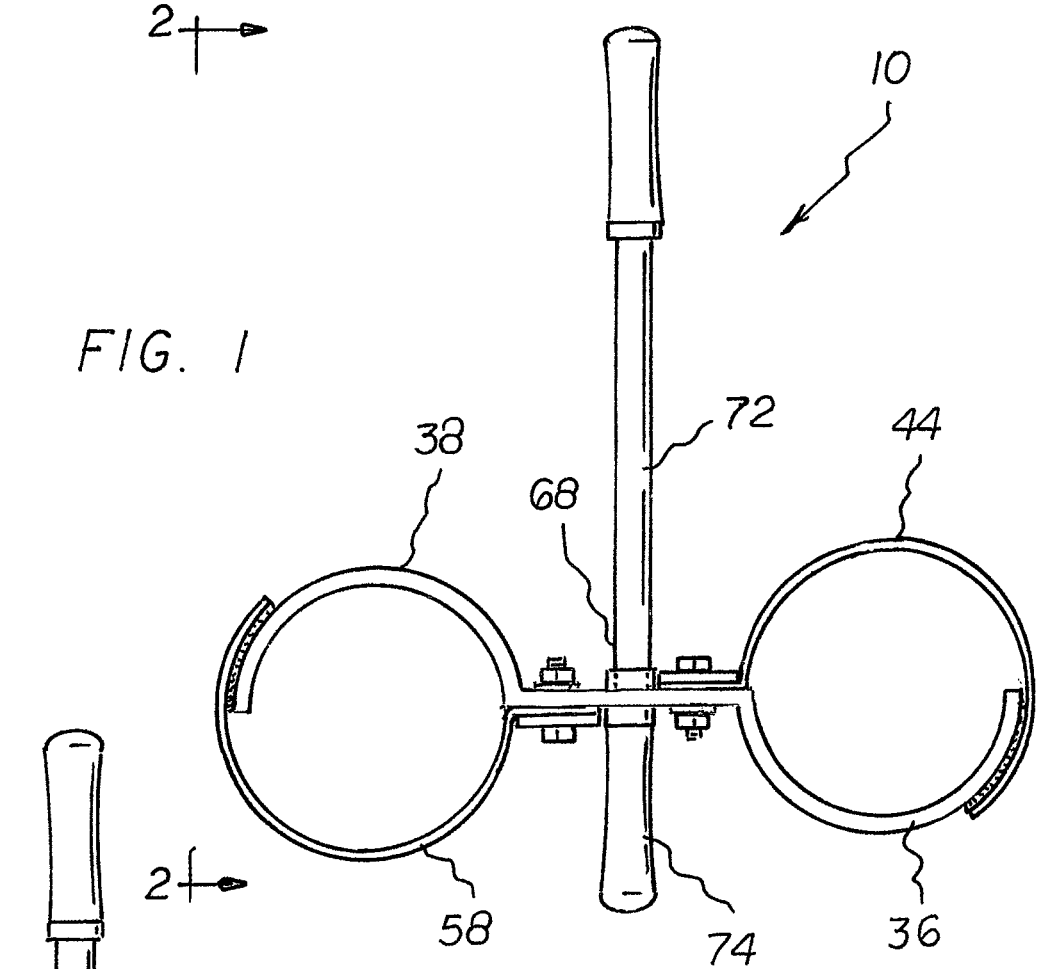
FIG. 1
FIG 2

SACROILIAC MANIPULATION SYSTEM

BACKGROUND OF THE INVENTION

Field of the Invention

The present invention relates to a sacroiliac manipulation system and more particularly pertains to self manual manipulation by a patient by coupling to legs of a patient for abating sacroiliac joint pain in a safe, convenient, and economical manner.

Description of the Prior Art

The use of sacroiliac manipulation systems of known designs and configurations is known in the prior art. More specifically, sacroiliac manipulation systems of known designs and configurations previously devised and utilized for the purpose of abating sacroiliac pain are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the prior art does not describe a sacroiliac manipulation system for self manual manipulation by a patient by coupling to legs of a patient for abating sacroiliac joint pain in a safe, convenient, and economical manner.

In this respect, the sacroiliac manipulation system according to the present invention substantially departs from the conventional concepts and designs of the prior art, and in doing so provides an apparatus primarily developed for the purpose of self manual manipulation by a patient by coupling to legs of a patient for abating sacroiliac joint pain in a safe, convenient, and economical manner.

Therefore, it can be appreciated that there exists a continuing need for a new and improved sacroiliac manipulation system which can be used for self manual manipulation by a patient by coupling to legs of a patient for abating sacroiliac joint pain in a safe, convenient, and economical manner. In this regard, the present invention substantially fulfills this need.

SUMMARY OF THE INVENTION

In view of the disadvantages inherent in the known types of sacroiliac manipulation systems of known designs and configurations now present in the prior art, the present invention provides an improved sacroiliac manipulation system. As such, the general purpose of the present invention, which will be described subsequently in greater detail, is to provide a new and improved sacroiliac manipulation system and method which has all the advantages of the prior art and none of the disadvantages.

To attain this, in a broad context, first provided is a base having an upwardly facing surface and a downwardly facing surface, an interior edge and an exterior edge, and a first end and a second end. The base has a central section in a rectangular configuration. The base has a first end section in a semi-cylindrical configuration. The first end section extends between the first end and the central section. The base has a second end section in a semi-cylindrical configuration. The second end section extends between the second end and the central section. First and second hook and loop patches are provided on the first and second end sections. First and second hook and loop straps are provided. Each hook and loop strap has a fixed end attached to the central section. Each hook and loop strap has a free end separably coupled to an associated hook and loop patch. Such components are individually configured and correlated with respect to each other so as to attain the desired objective.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including such equivalent constructions insofar as they do not depart from the spirit and scope of the present invention.

It is therefore an object of the present invention to provide a new and improved sacroiliac manipulation system which has all of the advantages of the prior art sacroiliac manipulation systems of known designs and configurations and none of the disadvantages.

It is another object of the present invention to provide a new and improved sacroiliac manipulation system which may be easily and efficiently manufactured and marketed.

It is a further object of the present invention to provide a new and improved sacroiliac manipulation system which is of durable and reliable constructions.

An even further object of the present invention is to provide a new and improved sacroiliac manipulation system which is susceptible of a low cost of manufacture with regard to both materials and labor, and which accordingly is then susceptible of low prices of sale to the consuming public, thereby making such sacroiliac manipulation system economically available to the buying public.

Lastly, it is an object of the present invention to provide a sacroiliac manipulation system for self manual manipulation by a patient by coupling to legs of a patent for abating sacroiliac joint pain in a safe, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front elevational view of a sacroiliac manipulation system constructed in accordance with the principles of the present invention.

FIG. 2 is a side elevational view of the system taken along line 2-2 of FIG. 1.

The same reference numerals refer to the same parts throughout the various Figures.

DESCRIPTION OF THE PREFERRED EMBODIMENT

Figure 3:
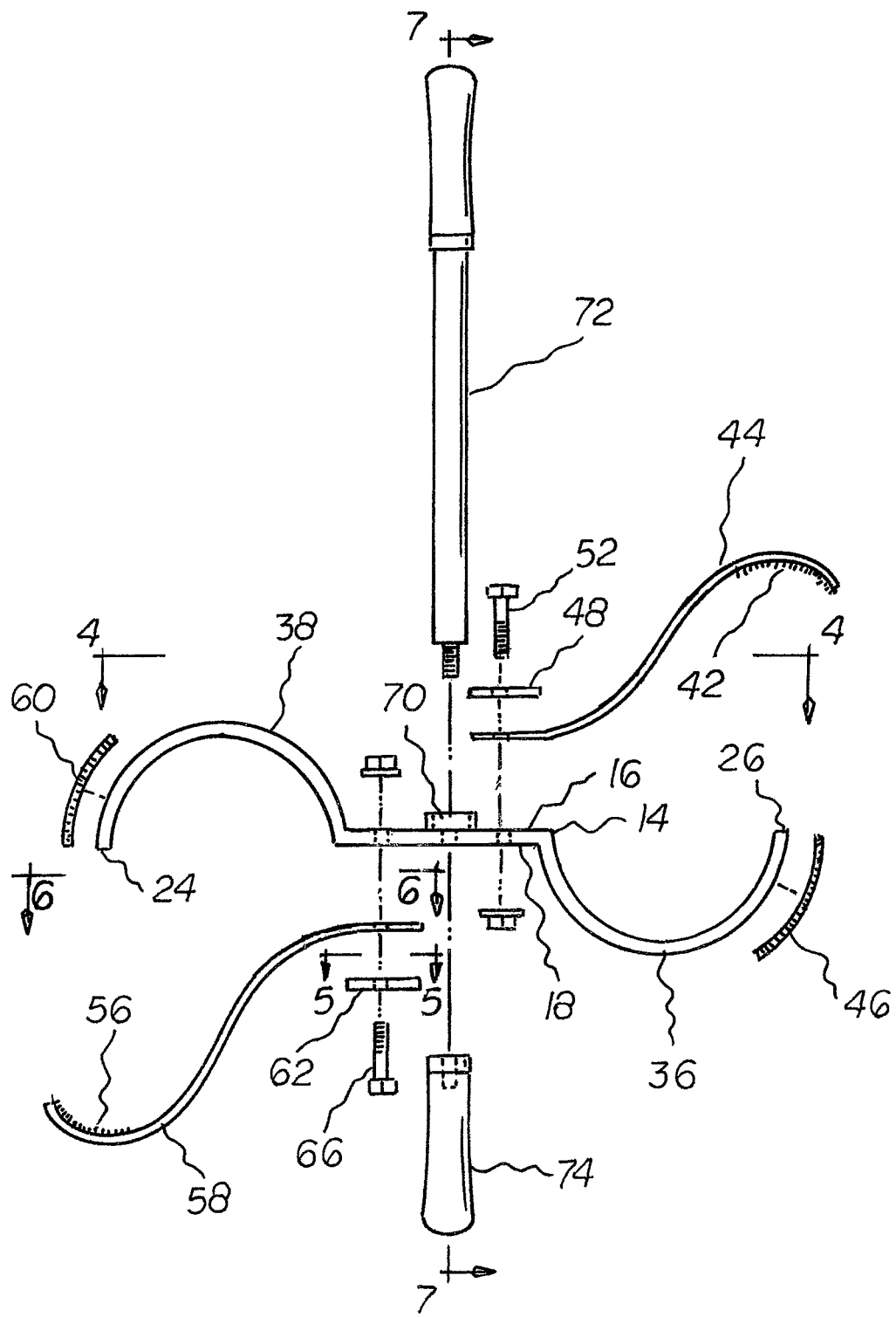
FIG. 3 is an exploded front elevational view of the system illustrated in the prior Figures.
Figure 4:
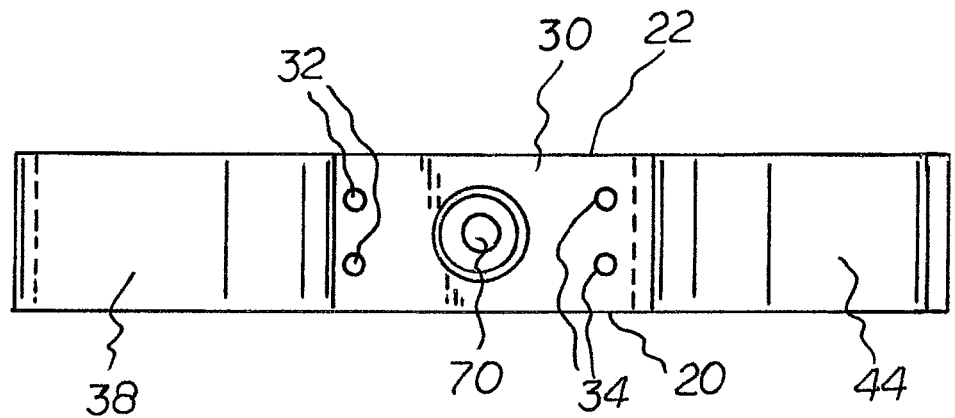
FIG. 4 is a plan view of a portion of the system taken along line 4-4 of FIG. 3.
Figure 5:
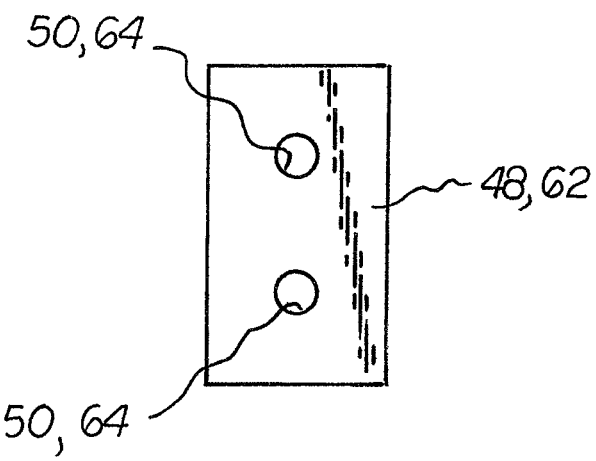
FIG. 5 is a plan view of a portion of the system taken along line 5-5 of FIG. 3.
Figure 6:
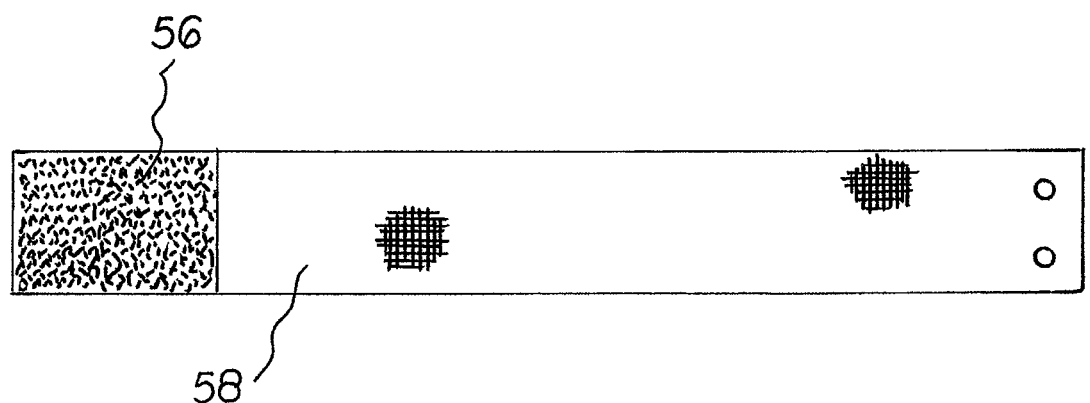
FIG. 6 is a plan view of a portion of the system taken along line 6-6 of FIG. 3.
Figure 7:
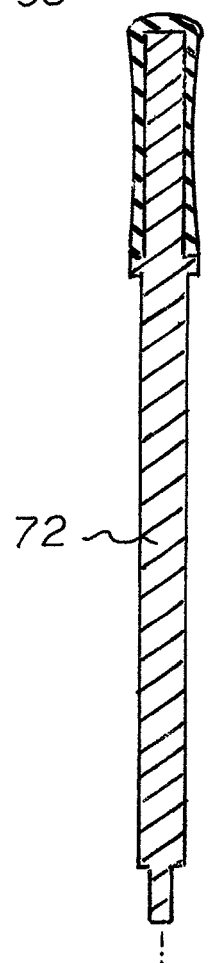
FIG. 7 is an exploded cross-sectional view taken along line 7-7 of FIG. 3.
Figure 7:
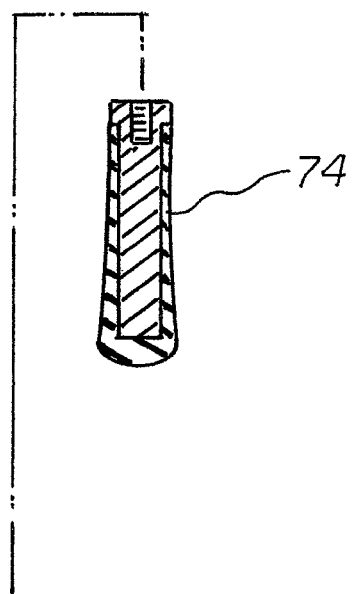

With reference now to the drawings, and in particular to FIG. 1 thereof, the preferred embodiment of the new and improved sacroiliac manipulation system embodying the principles and concepts of the present invention and generally designated by the reference numeral 10 will be described.

The present invention, the sacroiliac manipulation system 10 is comprised of a plurality of components. Such components are individually configured and correlated with respect to each other so as to attain the desired objective. In their broadest context such include a base, first and second hook and loop patches and first and second hook and loop straps.

From a specific perspective, the invention of the present application is In the preferred embodiment of the sacroiliac manipulation system for self manual manipulation by a patient by coupling to legs of a patient for abating sacroiliac joint pain, the coupling to the legs and the abating sacroiliac joint pain being done in a safe, convenient, and economical manner, designated by reference numeral 10, first provided is a base 14. The base has an upwardly facing surface 16 and a parallel downwardly facing surface 18 separated by a thickness of 0.50 inches, plus or minus 10 percent. The base has an interior edge 20 and a parallel exterior edge 22 separated by a width of 3.50 inches, plus or minus 10 percent. The base has a first end 24 and a parallel second end 26 separated by a length. The base is fabricated of rigid stainless steel metallic material.

The base has a central section 30 in a rectangular configuration. The central section is in a central plane. The first end and the second end are in the central plane. The central plane has a length of 7.5 inches, plus or minus 10 percent. Two first base holes 32 are laterally spaced and extend through the central section adjacent to the first end. Two second base holes 34 are laterally spaced and extend through the central section adjacent to the second end. The first base holes are spaced from the second base holes by a hole spacing of 5.5 inches.

The base has a first end section 36 in a downwardly extending semi-cylindrical configuration. The first end section extends between the first end and the central section adjacent to the first base holes. The first end section has a radius of curvature of 3.0 inches, plus or minus 10 percent.

The base has a second end section 38 in an upwardly extending semi-cylindrical configuration. The second end section extends between the second end and the central end section adjacent to the second base holes. The second end section has a radius of curvature of 3.0 inches, plus or minus 10 percent.

Next provided are a first hook and loop patch 42 and a first hook and loop strap 44. The first hook and loop patch covers the downwardly facing surface of the first end section. The first hook and loop strap 44 has a fixed end and a first free end separated by 20 inches, plus or minus 10 percent. The fixed end has laterally spaced first strap holes overlying the first base holes. A first supplemental hook and loop patch 46 on a portion of the first end section releasably couples to the first hook and loop patch. A first securement plate 48 having first securement plate holes 50 overlies the first strap holes. Threaded fasteners 52 extend through the first securement plate holes and the first strap holes and the first base holes. The first free end is removably couplable to the first hook and loop patch to restrain a first leg of a patient above a knee during therapy.

Next provided are a second hook and loop patch 56 and a second hook and loop strap 58. The second hook and loop patch 56 covers the upwardly facing surface of the second end section. The second hook and loop strap 58 has a fixed end and a second free end separated by 20 inches, plus or minus 10 percent. The fixed end has laterally spaced second strap holes overlying the second base holes. A second supplemental hook and loop patch 60 on a portion of the second end section releasably couples to the second hook and loop patch. A second securement plate 62 has second securement plate holes overlying the second strap holes. Threaded fasteners 66 extend through the second securement plate holes and the second strap holes and the second base holes. The second free end is removably couplable to the second hook and loop patch to restrain a second leg of a patient above a knee during therapy.

Provided lastly is a handling assembly 68 which includes an aperture 70 extending through a central extent of the base. The handling assembly also includes a longer component 72 and a shorter component 74. The longer component includes a grip above with a threaded projection extending down through the aperture. The shorter component includes a grip below with a threaded recess above removably receiving the threaded projection to facilitate handling the system.

The handling assembly functions to help stabilize the pushing and pulling of the legs. It also helps to release muscle tissue that would have scar tissue known as Fascia.

Sacroiliac joint pain is caused by instability in the joint. The sacroiliac joint is moving too much and causing irritation to the nerves that go to the joint. It is believed that the most effective relief can be achieved by combining exercise and manual manipulation. The present invention allows patients to do the manual manipulation themselves.

Following are instructions for use of the present invention: Strap the device around each leg just above the knee. Lie on your back and lift both left and right legs. While keeping the legs bent, one will have a push and pull sequence. Continuing to be on your back, place both feet on the ground with your knees bent and push legs apart. Finally maintaining the same position squeeze legs together. You will feel a release and feel relief.

Using this self sacroiliac manipulation tool, along with the proper exercise routine, and along with a user's manual provided with the sacroiliac manipulation system of the present invention, will eliminate sacroiliac joint pain.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A sacroiliac manipulation system comprising:
   a base having an upwardly facing surface and a downwardly facing surface, an interior edge and an exterior edge, a first end and a second end;
   the base having a central section in a rectangular configuration;
   the base having a first end section in a semi-cylindrical configuration, the first end section extending between the first end and the central section;
   the base having a second end section in a semi-cylindrical configuration, the second end section extending between the second end and the central section;
   first and second hook and loop patches on the first and second end sections;
   first and second hook and loop straps, each hook and loop strap having a fixed end attached to the central section, each hook and loop strap having a free end separably coupled to an associated hook and loop patch; and
   securement plates with threaded fasteners coupling the first and second hook and loop straps to the central section.

2. The system as set forth in claim 1 wherein the first end section extends downwardly and the second end section extends upwardly.

3. The system as set forth in claim 1 and further including:
   a handling assembly including an aperture extending through a central extent of the base, the handling assembly also including a longer component and a shorter component, the longer component including a grip above and a threaded projection below extending down through the aperture, the shorter component including a grip below and a threaded recess above removably receiving the threaded projection to facilitate handling the system.

4. A sacroiliac manipulation system (10) for coupling to legs of a patient for abating sacroiliac joint pain, the system comprising, in combination:
   a base (14) having an upwardly facing surface (16) and a parallel downwardly facing surface (18) separated by a thickness of 0.50 inches, plus or minus 10 percent, the base having an interior edge (20) and a parallel exterior edge (22) separated by a width of 3.50 inches, plus or minus 10 percent, the base having a first end (24) and a parallel second end (26) separated by a length, the base being fabricated of rigid stainless steel metallic material;
   the base having a central section (30) in a rectangular configuration, the central section being in a central plane, the first end and the second end being in the central plane, the central plane having a length of 7.5 inches, plus or minus 10 percent, two first base holes (32) laterally spaced and extending through the central section adjacent to the first end, two second base holes (34) laterally spaced and extending through the central section adjacent to the second end, the first base holes being spaced from the second base holes by a hole spacing of 5.5 inches;
   the base having a first end section (36) in a downwardly extending semi-cylindrical configuration, the first end section extending between the first end and the central section adjacent to the first base holes, the first end section having a radius of curvature of 3.0 inches, plus or minus 10 percent;
   the base having a second end section (38) in an upwardly extending semi-cylindrical configuration, the second end section extending between the second end and the central section adjacent to the second base holes, the second end section having a radius of curvature of 3.0 inches, plus or minus 10 percent;
   a first hook and loop patch (42) covering the downwardly facing surface of the first end section, a first hook and loop strap (44) having a fixed end and a first free end separated by 20 inches, plus or minus 10 percent, the fixed end having laterally spaced first strap holes overlying the first base holes, a first supplemental hook and loop patch (46) on a portion of the first end section releasably coupled to the first hook and loop patch, a first securement plate (48) having first securement plate holes (50) overlying the first strap holes, threaded fasteners (52) extending through the first securement plate holes and the first strap holes and the first base holes, the first free end being removably couplable to the first hook and loop patch to restrain a first leg of a patient above a knee during therapy;
   a second hook and loop patch (56) covering the upwardly facing surface of the second end section, a second hook and loop strap (58) having a fixed end and a second free end separated by 20 inches, plus or minus 10 percent, the fixed end having laterally spaced second strap holes (64) overlying the second base holes, a second supplemental hook and loop patch (60) on a portion of the second end section, a second securement plate (62) having second securement plate holes overlying the second strap holes, threaded fasteners (66) extending through the second securement plate holes and the second strap holes and the second base holes, the second free end being removably couplable to the second hook and loop patch to restrain a second leg of a patient above a knee during therapy; and
   a handling assembly (68) including an aperture (70) extending through a central extent of the base, the handling assembly also including a longer component (72) and a shorter component (74), the longer component including a grip above and a threaded projection below extending down through the aperture, the shorter component including a grip below and a threaded recess above removably receiving the threaded projection to facilitate handling the system.

* * * * *